United States Patent
Costabile

(10) Patent No.: US 10,143,567 B2
(45) Date of Patent: Dec. 4, 2018

(54) IMPLANTS AND GUIDES FOR INSERTING AN IMPLANT

(71) Applicant: Alphatec Spine, Inc., Carlsbad, CA (US)

(72) Inventor: Jonathan T. Costabile, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 15/273,847

(22) Filed: Sep. 23, 2016

(65) Prior Publication Data

US 2017/0079805 A1    Mar. 23, 2017

Related U.S. Application Data

(60) Provisional application No. 62/222,552, filed on Sep. 23, 2015.

(51) Int. Cl.
| | | |
|---|---|---|
| *A61F 2/30* | (2006.01) | |
| *A61F 2/44* | (2006.01) | |
| *A61F 2/46* | (2006.01) | |
| *A61F 2/28* | (2006.01) | |

(52) U.S. Cl.
CPC .......... *A61F 2/447* (2013.01); *A61F 2/30771* (2013.01); *A61F 2/4611* (2013.01); *A61F 2002/2835* (2013.01); *A61F 2002/30827* (2013.01); *A61F 2002/30828* (2013.01); *A61F 2002/30904* (2013.01); *A61F 2002/4622* (2013.01); *A61F 2002/4627* (2013.01); *A61F 2002/4687* (2013.01)

(58) Field of Classification Search
CPC .... A61F 2/447; A61F 2/30771; A61F 2/4611; A61F 2002/2835; A61F 2002/30827; A61F 2002/30828; A61F 2002/30904; A61F 2002/4622; A61F 2002/4627; A61F 2002/4387
USPC ....... 623/17.11–17.16; 606/246–279, 99, 96, 606/100, 86 R, 86 A
See application file for complete search history.

(56) References Cited

U.S. PATENT DOCUMENTS

| | | | | |
|---|---|---|---|---|
| 7,575,576 | B2* | 8/2009 | Zubok | A61F 2/442 606/86 A |
| 7,951,202 | B2* | 5/2011 | Ralph | A61B 17/025 623/17.11 |
| 2002/0116009 | A1* | 8/2002 | Fraser | A61F 2/4611 606/99 |
| 2004/0225295 | A1* | 11/2004 | Zubok | A61F 2/442 606/90 |
| 2005/0165408 | A1* | 7/2005 | Puno | A61F 2/4611 606/99 |
| 2010/0076557 | A1* | 3/2010 | Miller | A61F 2/4465 623/17.11 |

(Continued)

*Primary Examiner* — Pedro Philogene
(74) *Attorney, Agent, or Firm* — Honigman Miller Schwartz and Cohn LLP

(57) ABSTRACT

A system and a method for performing a spinal procedure configured to minimize the size of the surgical corridor so as to reduce recovery time is provided. The system and method include an implant and a guide. The guide is configured to be disposed within a surgical corridor formed by an instrument. The instrument is removed wherein the muscles may contract onto the guide so as to reduce the surgical corridor, wherein the implant is slid down the surgical corridor between a pair of guide members.

4 Claims, 13 Drawing Sheets

(56) References Cited

U.S. PATENT DOCUMENTS

2010/0160983 A1* 6/2010 Runco .................. A61F 2/4611
                 606/86 A
2014/0330383 A1* 11/2014 Wimberley ........... A61F 2/4465
                 623/17.16
2014/0343559 A1* 11/2014 Flickinger ............ A61B 17/025
                 606/90

* cited by examiner

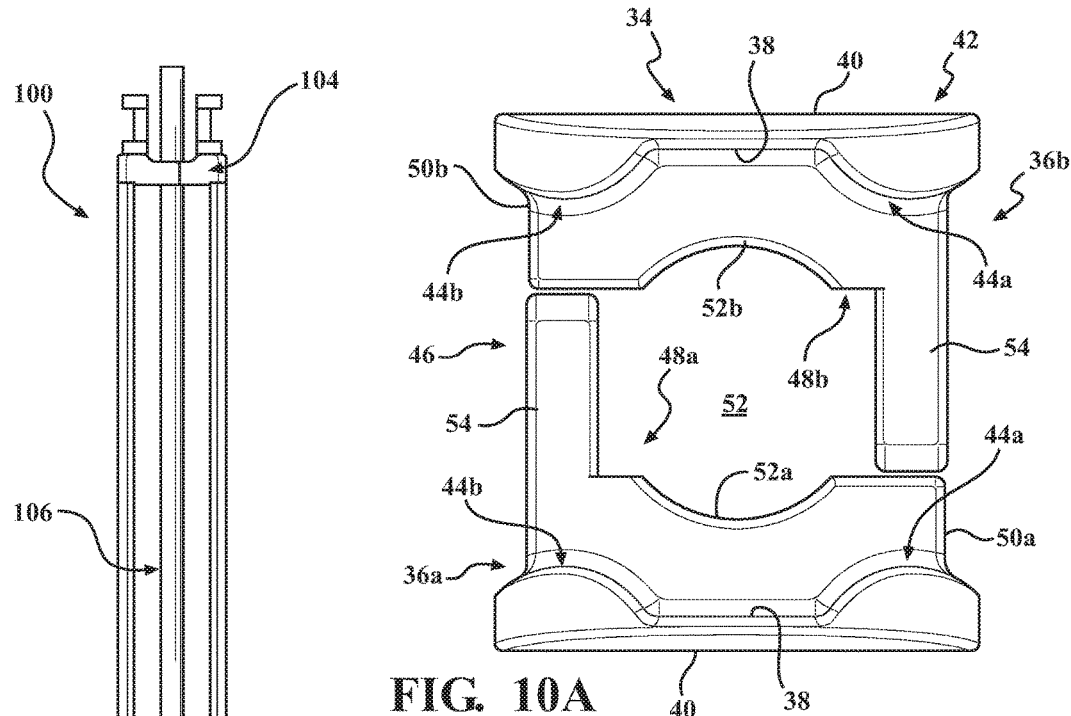
FIG. 10A
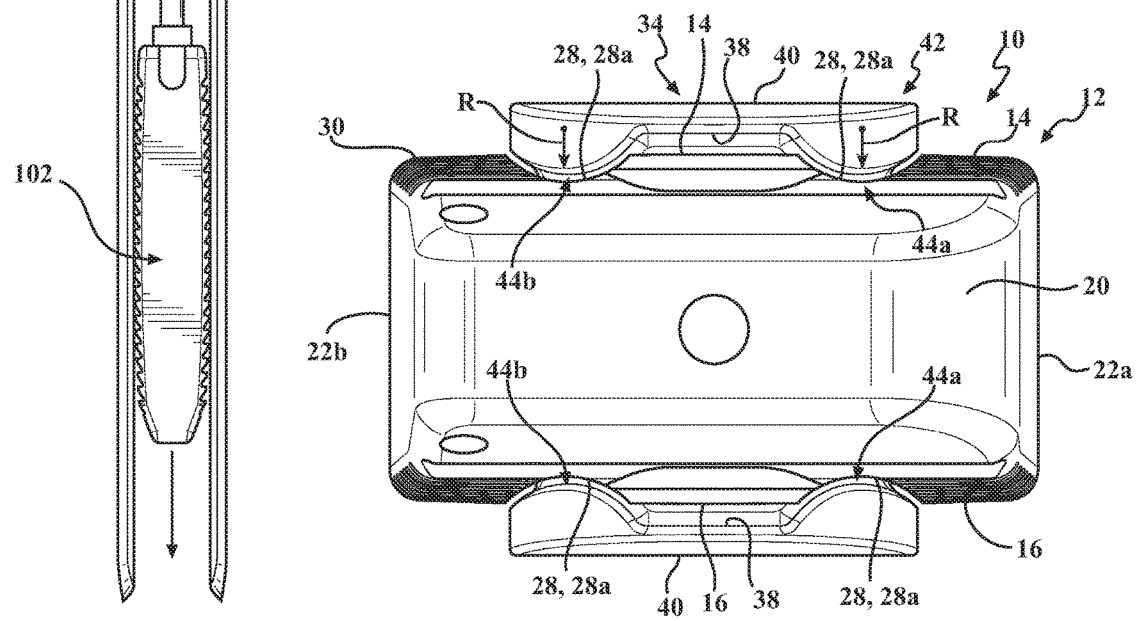
FIG. 9
FIG. 10B

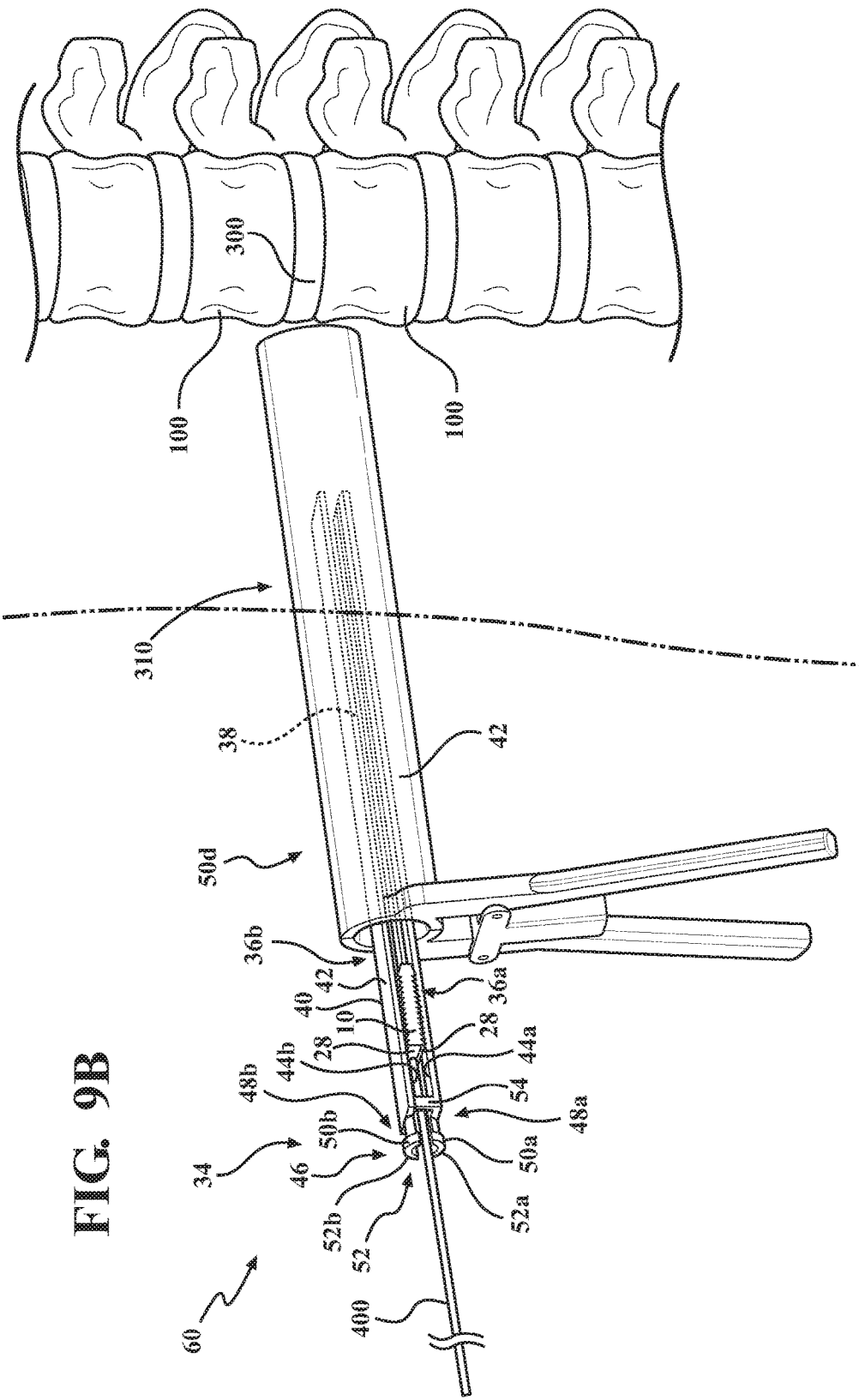

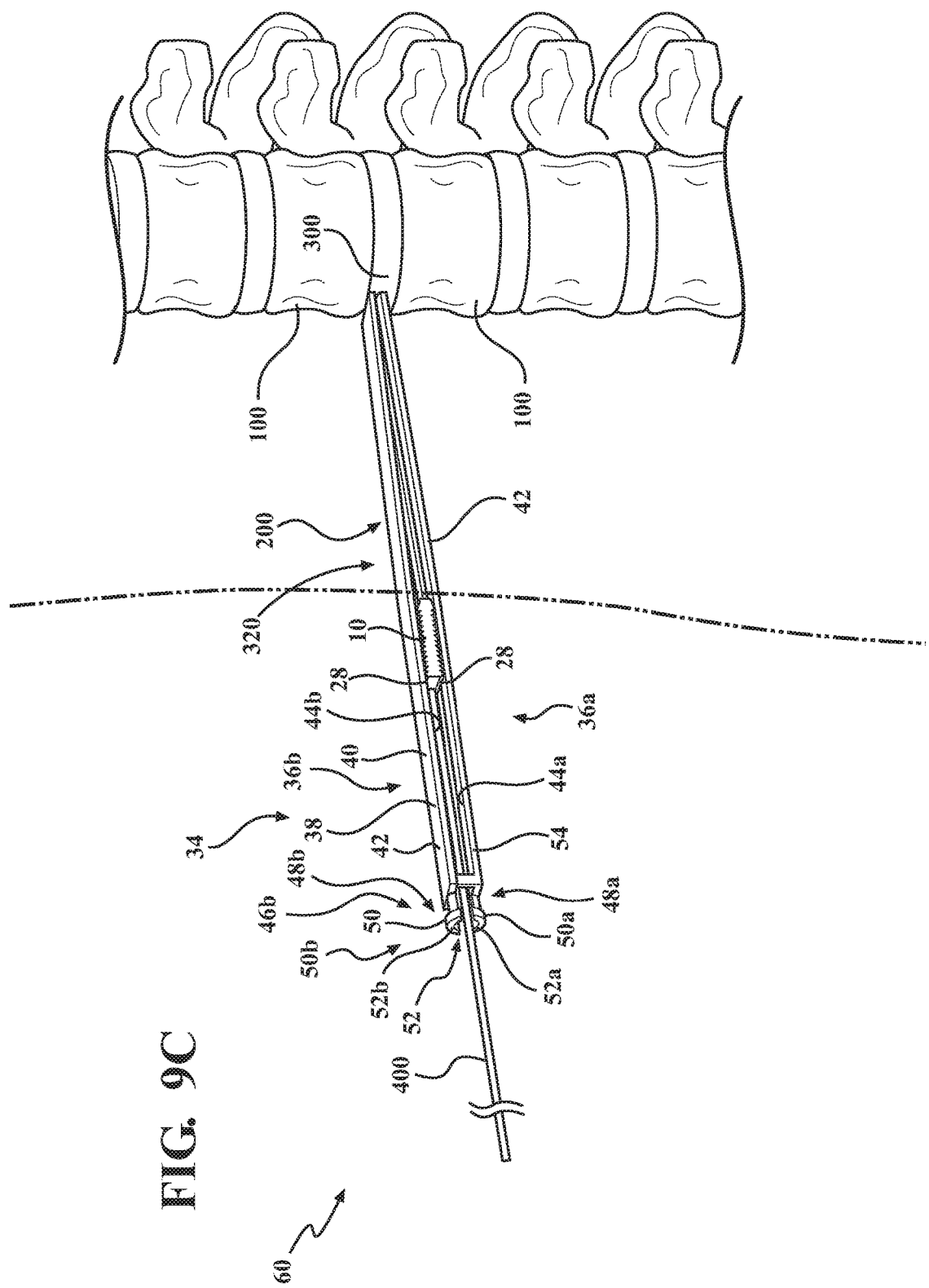

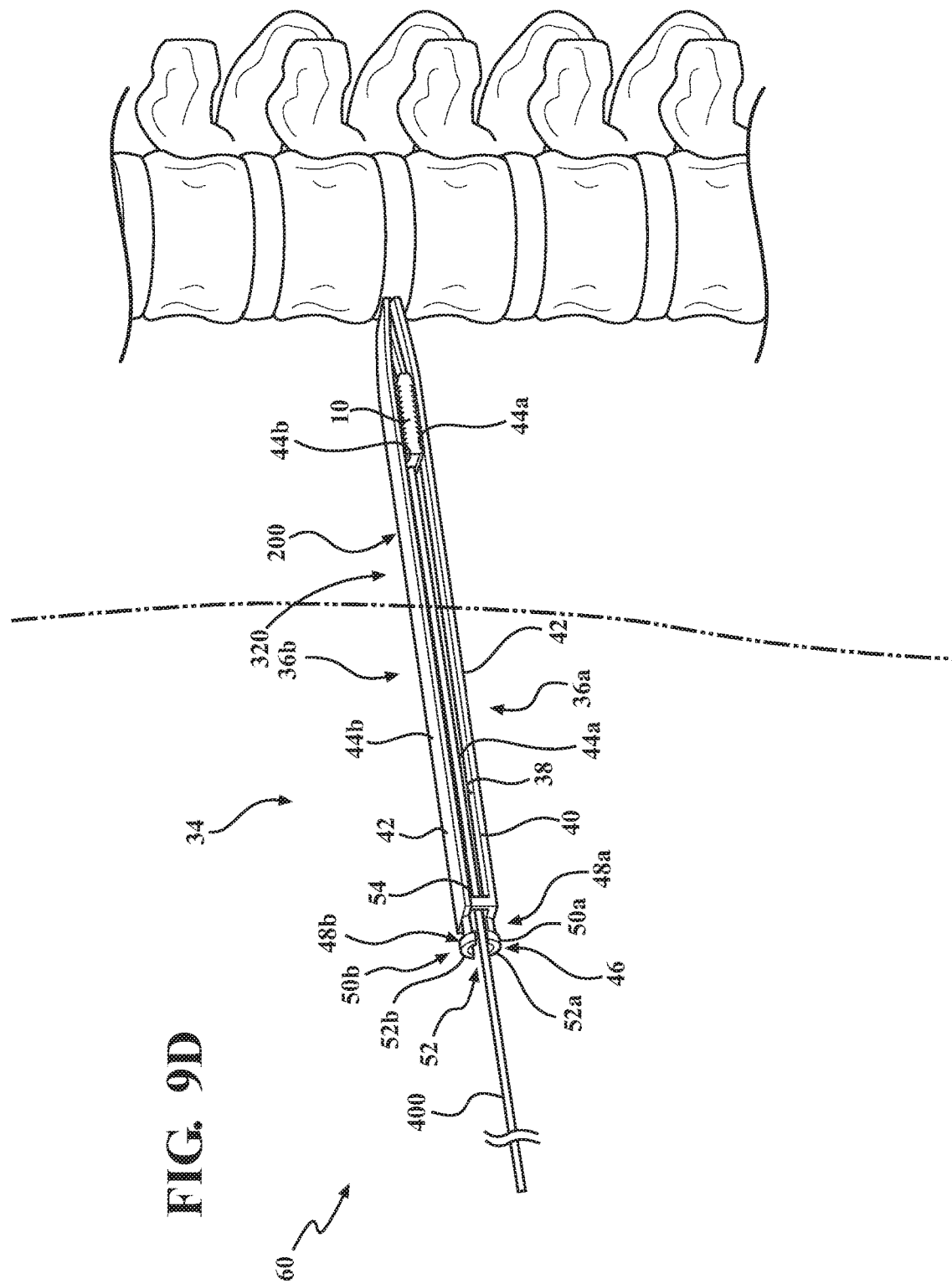

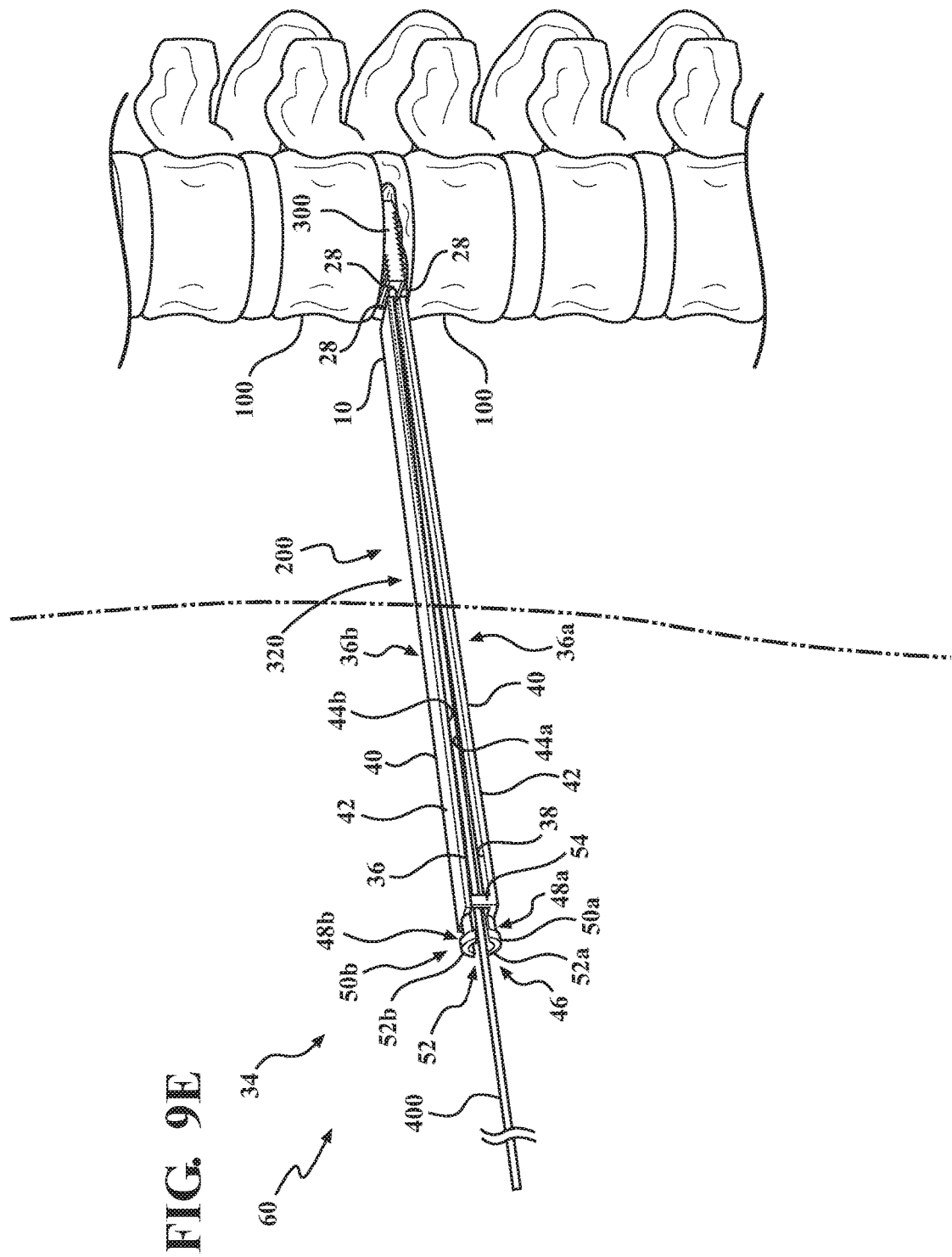

IMPLANTS AND GUIDES FOR INSERTING AN IMPLANT

CROSS-REFERENCE TO RELATED APPLICATIONS

This application claims priority of U.S. Provisional Patent Application No. 62/222,552 filed Sep. 23, 2015, the contents of which are incorporated herein by reference.

FIELD OF THE INVENTION

An implant, a guide for inserting the implant, and a system and method for inserting an implant in a surgical corridor so as to reduce recovery time for a patient are provided.

BACKGROUND OF THE INVENTION

Minimally invasive spinal surgeries are known. Such procedures include an implant directed to be inserted between a pair of adjacent vertebrae. The insertion of the implant is done through a surgical corridor which is formed by an instrument such as a retractor with retractor blades. The surgical corridor is dimensioned to allow the implant to pass through so as to place the implant into a surgical site. Accordingly, the retractor blades hold the muscles apart for the duration of the implant process.

However, it is known that the extension of muscle at a surgical site for a prolonged period of time has a direct relationship to the recovery time for a patient. In particular, the longer the retractor holds the muscles apart the longer the recovery time. The muscles are held apart to form the surgical corridor for not only the period of time needed to insert the implant into the surgical site, but also the time to fill the space within the implant body with bone graft material. Accordingly, it remains desirable to have a guide configured to reduce the expansion time of the muscles so as to minimize recovery time.

Further, current retractors provide a surgical corridor for which the implant is passed through. The surgical corridor provides a predetermined amount of tolerance between the inner surface of the retractor blades and the outer surface of the implant. Thus, the surgeon passes the implant through the surgical corridor free handed. Accordingly, it remains desirable to have a guide configured to retain the implant along an axial path of the surgical corridor towards the surgical site.

SUMMARY OF THE INVENTION

An implant having a body with a pair of grooves on superior and inferior surfaces of the implant is provided. The implant is adaptable for use with a guide. The guide includes a pair of guide members and a clasping mechanism. Each guide member includes an elongated member. The clasping mechanism is disposed on the proximal ends of the elongated members. The clasping mechanism is configured to hold the pair of elongated members together such that the proximal ends of the guide are spaced apart from each other a predetermined distance.

The elongated members further include a pair of ribs extending axially on opposite sides. The ribs are formed on respective inner surfaces of the guide members and are configured to engage corresponding grooves on the superior and inferior surfaces of the implant.

The clasping mechanism includes a pair of clasping members configured work together to maintain a spatial distance between proximal ends of the respective guide members. The clasping members are further dimensioned so as to form a through hole for which an inserter may be passed through.

A system and method for inserting an implant into a surgical site through a surgical corridor is also provided. The system includes an implant having a body with a pair of grooves. The pair of grooves may be on one or one both of the superior and inferior surfaces of the implant. The system further includes a guide. The implant is adaptable for use with the guide. The guide includes a pair of guide members and a clasping mechanism. Each guide member includes an elongated member. The clasping mechanism is disposed on the proximal ends of the elongated members. The clasping mechanism is configured to hold the pair of elongated members together such that the proximal ends of the guide are spaced apart from each other a predetermined distance.

The elongated members further include a pair of ribs extending axially on opposite sides. The ribs are formed on respective inner surfaces of the guide members and are configured to engage corresponding grooves on the superior and inferior surfaces of the implant.

The clasping mechanism includes a pair of clasping members configured to fit together and maintain a spatial distance between proximal ends of the respective guide members. The clasping members are further dimensioned so as to form a through hole for which an inserter may be passed through.

The method includes the step of inserting the guide members into a surgical corridor formed by a retractor. The retractor may be pulled from the surgical corridor wherein the muscle tissues are allowed to close in on the distal ends of the guide members, reducing muscle expansion around the surgical site. The implant is placed at the proximal end of the guide between the guide members so as to align the ribs of the guide member along respective grooves of the superior and inferior surfaces of the implant.

The method includes the step of passing an inserter through the through hole of the clasping member and pushing the implant down the surgical corridor towards the surgical site wherein the implant opens the surgical corridor as the implant moves towards the surgical site, thus reducing the exposure of the muscle in an expanded state and thereby reducing recovery time.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIG. 9 is a side view of an implant being pushed through a surgical corridor defined by a pair of guide members;

FIG. 9B is a view showing a guide with a pair of guide members inserted between retractor blades into the surgical corridor formed by the retractor and an implant between the pair of guide members;

FIG. 9C is a view showing the retractor shown in FIG. 9B removed from the surgical corridor and the implant advancing further down surgical corridor provided by the guide towards a surgical site;

FIG. 9D is a view showing the implant advancing further down the surgical corridor towards the surgical site relative to FIG. 9C;

FIG. 9E is a view showing the implant implanted in the surgical site;

FIG. 10a is a view from the distal end of the pair of guides looking towards the proximal end;

FIG. 10b is a view of FIG. 9 taken from the distal end of the pair of guide members;

DETAILED DESCRIPTION OF THE PREFERRED EMBODIMENTS

An implant configured to be guided along a surgical corridor is provided. The implant includes an implant body having a superior surface and an inferior surface, a pair of side walls and a distal end opposite a proximal end. The superior and inferior surfaces may be tapered on respective distal and proximal ends of the implant body.

The implant includes a catching feature configured to help engage the implant to adjacent vertebrae. In one embodiment, the catching feature is a plurality of ridges formed on opposite superior and inferior sides of the body. The sides of the body are shown generally smooth. In one embodiment, the superior and inferior sides of the body include a pair of grooves. The grooves extend axially along adjacent sides of the superior and inferior surfaces of the implant.

The implant includes at least one biologic cavity configured to store biological bone growth material. The biological cavities may be divided by inner walls which extend between opposite sides of the implant body. Bone graft material may be inserted into the biological cavity during the course of the spinal procedure so as to help the implant retain its position between adjacent vertebrae.

As used herein, the term distal refers to the end of an implant or instrument configured to move towards a surgical site whereas the proximal end is the end opposite the distal end. As used herein, a surgical site refers to the location in which an implant is to be inserted. For illustrative purposes, here the implant is used in minimally invasive spinal surgeries. Accordingly, the surgical site is a space between adjacent vertebrae. A surgical corridor refers to an elongated opening made in the body which provides a passage within the body to the surgical site.

A guide having a pair of guide members is also provided. The guide members are configured to be assembled together about their proximal end so as to be spaced apart and form a surgical corridor. The guide members include a guide body which is a generally elongated member. The guide members have an exterior surface and an interior surface. The interior surface is in open communication with the surgical corridor. In one embodiment, the interior surface of both guide members includes a pair of ribs extending axially along opposing sides of the guide members.

A clasping mechanism is disposed on the proximal end of the guide. The clasping mechanism is configured to secure the proximal ends of the guide members together. The clasping mechanism includes a pair of clasping members. Each clasping member includes one half of a concentric bore so as to form a through hole when the clasping members are engaged. The through hole is configured for a rod of an inserter to fit within and slide through.

Figure 1:
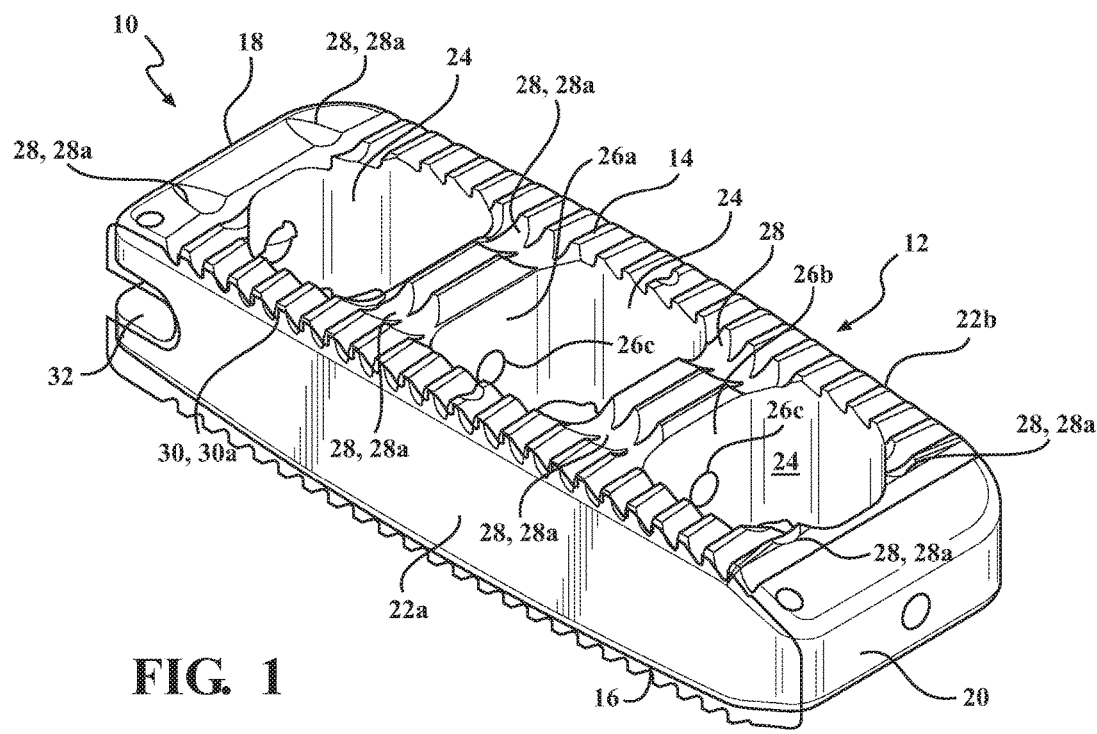
FIG. 1 is a perspective view showing the superior side of the implant.

With reference now to FIG. 1, an illustrative view of the implant 10 is provided. The implant 10 includes an implant body 12 having a superior surface 14 opposite an inferior surface 16, a proximal end 18 opposite a distal end 20, and a pair of sidewalls 22a, 22b opposite from each other. The distal and proximal ends 18, 20 of the implant body 12 may be tapered so as to facilitate the insertion of the implant 10 between adjacent vertebrae 100 (FIGS. 9C-9E). The implant 10 further includes a biological cavity 24 for holding biological material such as bone graft.

FIG. 1 provides an illustrative view of the superior surface 14 of the implant 10. However, it should be appreciated that the inferior surface 16 of the implant 10 may be identical to the superior surface 14 of the implant 10, namely the superior surface 14 of the implant 10 shows a pair of grooves 28 formed along an axis extending from a distal end 20 to a proximal end 18 of the implant body 12. The grooves 28 are formed by a plurality of generally tubular depressions 28a formed on respective superior and inferior surfaces 14, 16 of the implant body 12. Each of the generally tubular depressions 28a are axially aligned with each other so as to form a groove on each side and on each superior and inferior surface 14, 16 of the implant 10.

The grooves 28 are formed along the entire length of the implant body 12.

The implant 10 is shown as having three biological cavities 24 which bone growth material may fill. However, it should be appreciated that the implant 10 may have one or more biological cavities 24. The biological cavities 24 are defined by two inner walls 26a, 26b spaced apart from each other and extending between sidewalls 22a and 22b. The inner walls 26a, 26b may include an aperture 26c for receiving bone growth material.

Figure 4:
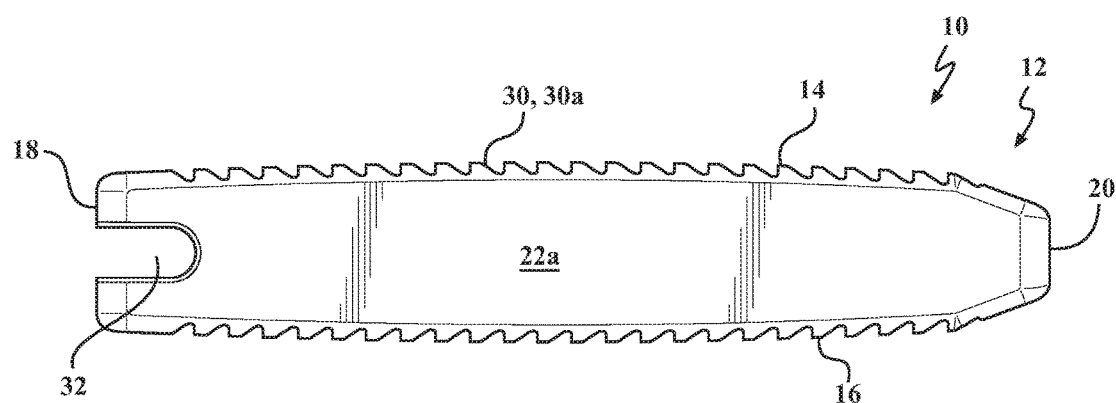
FIG. 4 is a side view of the implant shown in FIG. 1.

The implant 10 further includes a catching feature 30 configured to help engage the implant 10 to adjacent vertebra. In one embodiment, the catching feature 30 is a plurality of ridges 30a. The ridges 30a extend across the width of the implant body 12 on both the superior and inferior surfaces 14, 16. The ridges 30a are illustratively shown as having a sloped face to facilitate the introduction of the implant 10 into the surgical site 200 (FIG. 4). The ridges 30a further provide traction to help maintain the implant 10 between adjacent vertebrae 100.

The proximal end 18 of the implant 10 includes a catch 32 dimensioned to receive a head 402 of an inserter 400 (shown in FIG. 8B) so as to facilitate the push of the implant 10 along a surgical corridor 320. The catch 32 is illustratively shown as being a slot extending between the sidewalls 22a, 22*b* of the implant body 12 and generally equidistant between the superior and inferior surfaces 14, 16 of the implant body 12.

Figure 2:
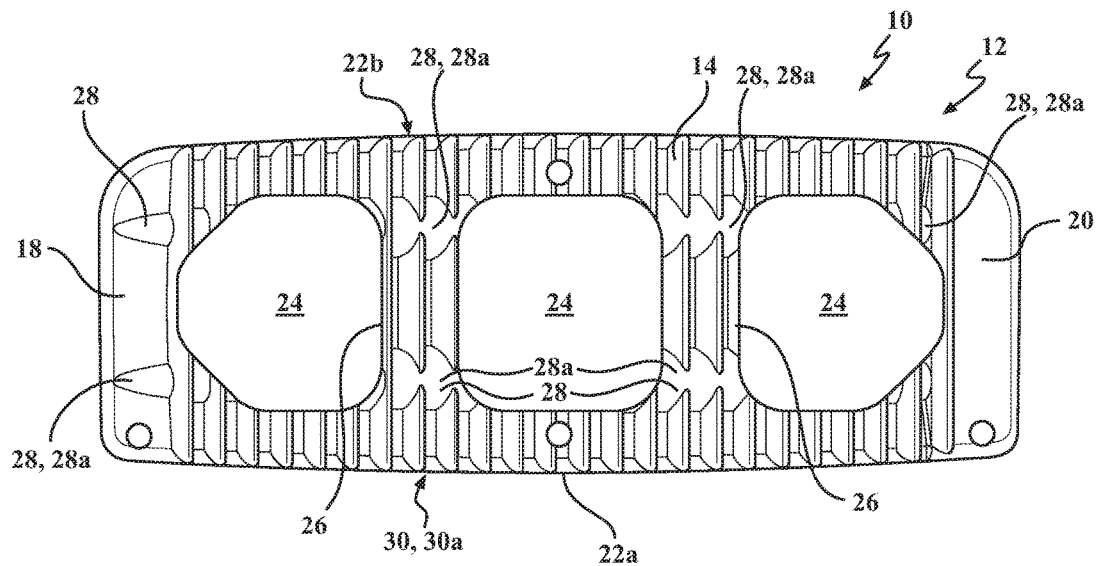
FIG. 2 is a top-down view of the implant shown in FIG. 1.
Figure 3:
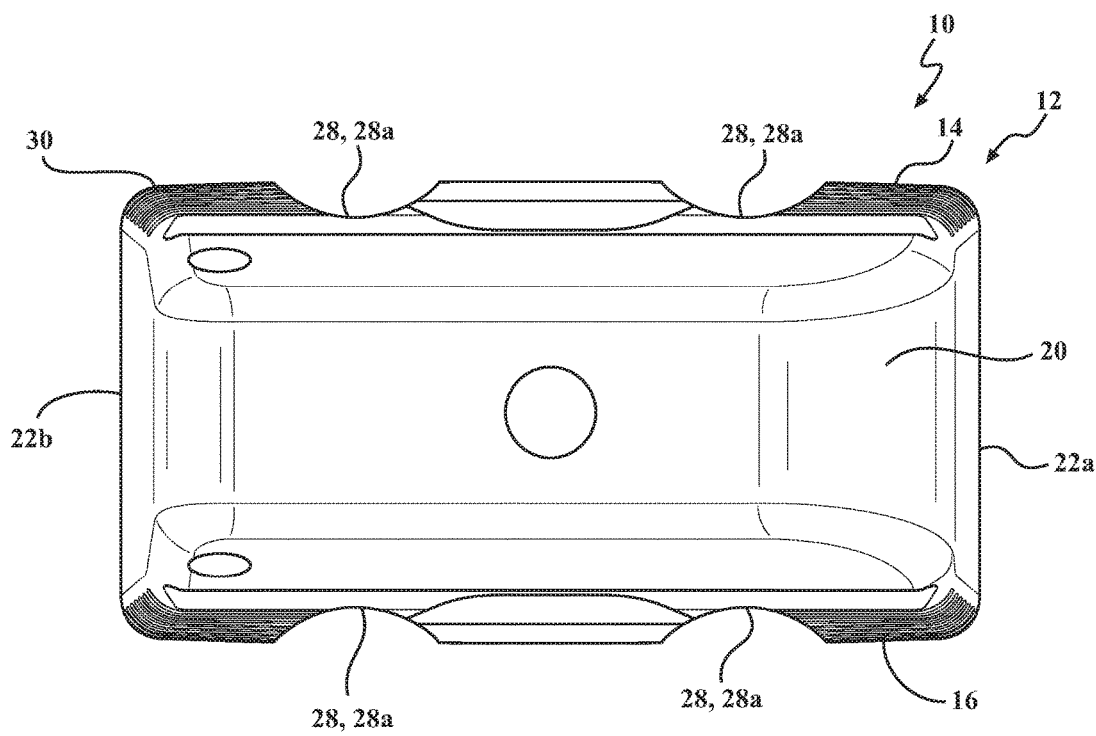
FIG. 3 is a frontal view of the implant shown in FIG. 1.

FIG. 2 shows a top-down view of the superior surface 14 shown in FIG. 1. As seen, the grooves 28 are formed along the side walls 22*a*, 22*b* of the implant 10. The grooves 28 are also formed on the inner walls 26*a*, 26*b* of the implant body 12. FIG. 3 is a frontal view of the implant 10 showing the grooves 28 formed along the superior and inferior surfaces 14, 16 of the implant body 12. FIG. 3 also shows how the grooves 28 form a C shaped cross-section having a generally uniform radius, wherein FIG. 2 shows how the circumferential surface of each of the tubular depressions 28*a* forming the grooves 28 change in length based upon the contours of the respective superior and inferior surfaces 14, 16 of the implant body 12.

FIG. 4 is a side view of the implant 10 showing the catch 32 disposed on the proximal end 18 of the implant 10. FIG. 4 also shows how the distal end 20 of the implant 10 is tapered, giving the implant 10 a generally bullet shape. The tapered end facilitates wedging of the implant 10 between adjacent vertebrae 100 (FIG. 9E). The ridges 30*a* are shown on both the superior and inferior surfaces 14, 16 of the implant 10.

Figure 5:
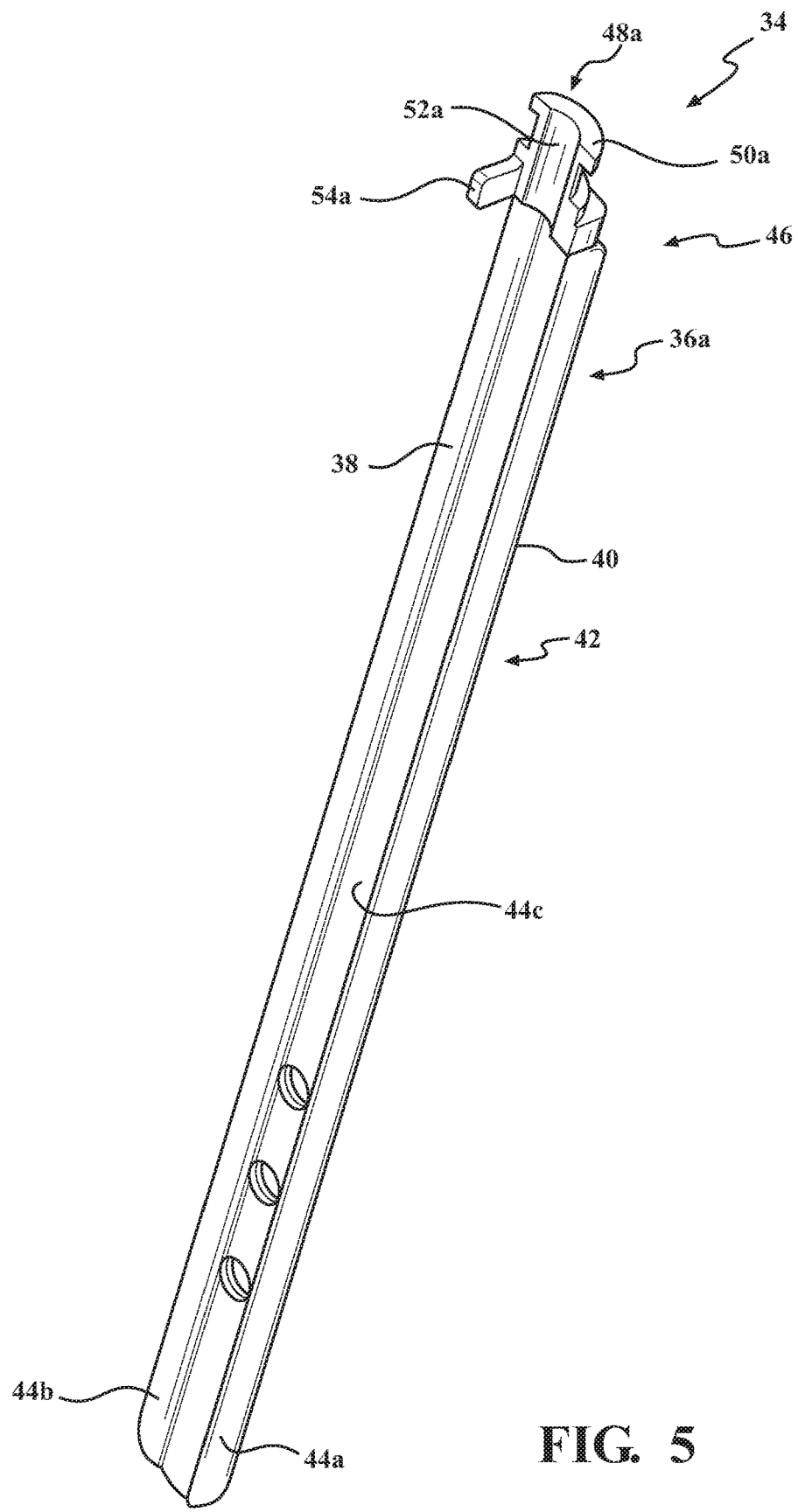
FIG. 5 is an interior view of one of the pair of guide members.
Figure 6:
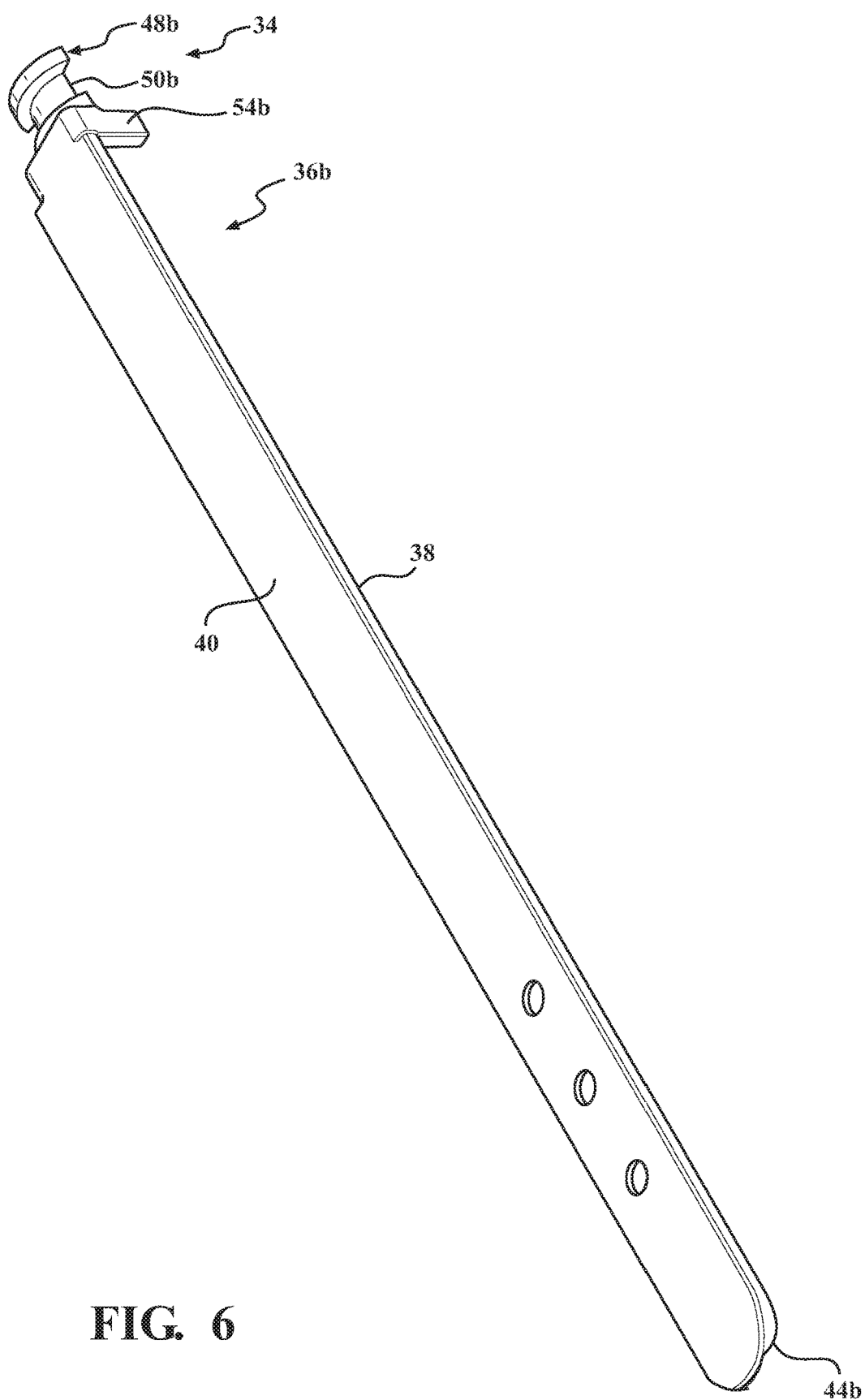
FIG. 6 is a view of the outer surface of the guide shown in FIG. 5.
Figures 7, 8:
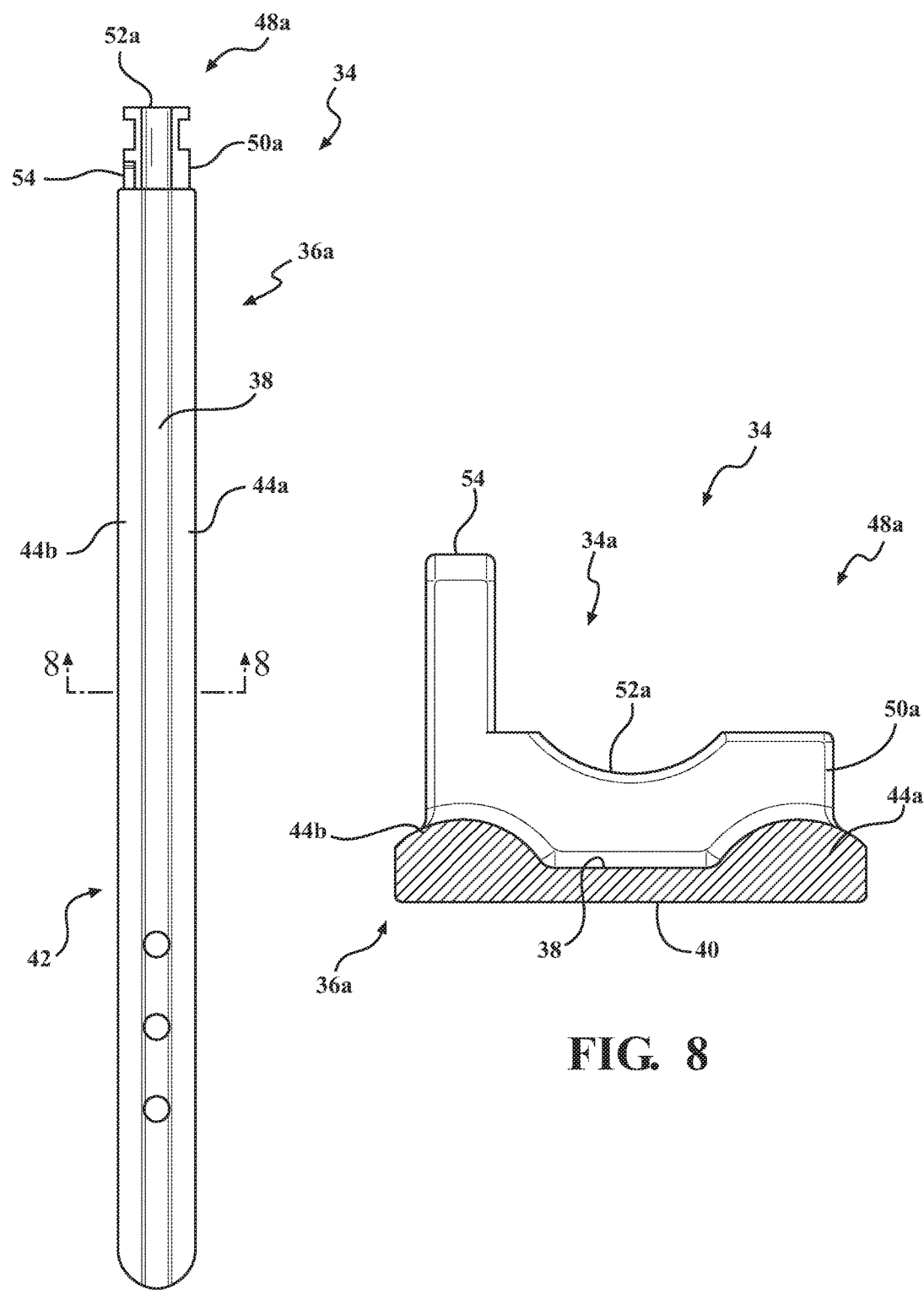
FIG. 7 is a top-down view showing the inner surface of the guide of FIG. 5.
FIG. 8 is a cross-sectional view taken along lines 8-8 of FIG. 7.

With reference now to FIGS. 5, 6, 7, 8A-8B, 9, 9A-9E, and 10, an illustrative embodiment of a guide 34 is provided. The guide 34 includes a pair of guide members 36*a*, 36*b*. Each of the guide members 36*a*, 36*b* is a generally elongated member. FIG. 5 shows one of the pair of guide members 36*a* and FIG. 6 shows the other of the pair of guide members 36*b*. The guide members 36*a*, 36*b* may be formed of a resilient and durable material such as titanium. The guide members 36*a*, 36*b* have an inner surface 38 opposite an outer surface 40. The inner surface 38 forms the surgical corridor 320 (FIG. 8B).

A view of the inner surface 38 is shown in FIG. 5, and the outer surface 40 is shown in FIG. 6. The guide members 36*a*, 36*b* include an elongated body 42 having a pair of ribs 44*a*, 44*b* disposed along opposite sides of the elongated body 42 so as to form an elongated groove 44*c*. The ribs 44*a*, 44*b* extend the axial length of the elongated body 42.

The guide 34 further includes a clasping mechanism 46 disposed on the proximal end of the guide 34. The clasping mechanism 46 is configured to couple the proximal ends of the guide members 36*a*, 36*b* together and also provide a bore through which an inserter may pass. In one embodiment of a clasping mechanism 46, the clasping mechanism 46 includes a pair of clasping members 48*a*, 48*b* coupled together or engaged so as to form a generally cylindrical body 50 having a through hole 52 (FIGS. 9C and 10*a*). The clasping mechanism 46 is configured to hold the proximal ends of the guide 34 together, and to accommodate the passage of the inserter 400 (e.g., shown in FIGS. 8B and 9C). Accordingly, the distal ends of the guide 34 are not supported. In particular, the distal ends of the guide members 36*a*, 36*b* are free to move relative to each other. The distal ends of the guide members 36*a*, 36*b* may be sharpened to help the guide 34 find purchase in between adjacent vertebrae 100.

FIG. 5 is a view taken of the inner surface 38 of one of the pair of guide members 36 showing one of the pair of clasping members 48*a*. The clasping member 48*a* includes a first cylindrical body portion 50*a* defining generally one half of the cylindrical body 50 and a first through hole portion 52*a* forming one half of the through hole 52. It should be appreciated that clasping member 48*b* is configured to engage clasping member 48*a* so as to form the generally cylindrical body 50 having the through hole 52, and thus clasping member 48*b* includes a second cylindrical body portion 50*b* forming the other half of the cylindrical body 50 and a second through hole portion 52*b* forming the other half of through hole 52. That is, first cylindrical body portion 50*a* forms one half of a concentric bore and the second cylindrical body portion 50*b* forms another half of a concentric bore, the two halves of the concentric bore forming the through hole 52.

The clasping members 48*a*, 48*b* further includes a spacer 54*a*, 54*b*, respectively, extending from an inner concave portion of the respective first and second cylindrical body portion 50*a*, 50*b*. The spacer 54*b* is located on an opposite side of the through hole 52 (FIG. 10*a*) from the spacer 54*a* shown in FIG. 5. Thus, engagement of the clasping members 48*a*, 48*b* when placed together space the elongated body 42 of respective guide members 36*a*, 36*b* apart from each other to form the surgical corridor 320. The spacers 54*a*, 54*b* are configured to abut against opposing surfaces of respective second and first cylindrical body portions 50*b*, 50*a* so as to maintain the proximal end of the guide members 36*a*, 36*b* apart from each other and yet allow the distal ends of the guide members 36*a*, 36*b* to close in on each other.

With reference to FIG. 10*a*, a view of the pair of guide members 36*a*, 36*b* assembled together and viewed from the distal end of the guide 34 is provided. FIG. 10*a* shows the pair of guide members 36*a*, 36*b* wherein the clasping members 48*a*, 48*b* are fitted together and the surgical corridor 320 is formed. As seen, the four ribs 44*a*, 44*b* are shown. One pair of ribs 44*a*, 44*b* are disposed on the first guide member 36*a* and one pair of ribs 44*a*, 44*b* are disposed on the second guide member 36*b*. FIG. 10*a* also provides a view of the through hole 52.

FIG. 10*b* is a view of FIG. 9 taken from the distal end of the pair of guide members 36*a*, 36*b*. FIG. 10*b* shows each rib 44*a*, 44*b* engaging respective grooves 28, 28*a*. Each rib 44*a*, 44*b* is dimensioned so as to be longer than the depth of the respective grooves 28, 28*a*. In one embodiment, the ribs have a convex outer surface so as to have a radius R which is longer than the depth of the respective groove 28, 28*a* so as to position the outer surface 14, 16 of the implant 10, in particular the superior surface 14 and inferior surface 16, apart from the inner surface 38 of the elongated body 42 of respective guide members 36*a*, 36*b*. Thus, movement of the implant 10 along the surgical corridor 320 is conducted by the sliding engagement of the ribs 44*a*, 44*b* with respect to the grooves 28, 28*a*. In other words, the superior 14 and inferior surfaces 14, 16 do not slide against the inner surface 38 of the respective guide members 36*a*, 36*b* as the implant 10 is pushed down the surgical corridor 320.

For illustrative purposes, the ribs 44*a*, 44*b* are shown on the outer sides of each guide member 36*a*, 36*b*, and the implant 10 is wider than the guide members 36*a*, 36*b*. However, it should be appreciated that the implant 10 may be dimensioned so as to be narrower than the guide members 36*a*, 36*b*.

Figure 11:
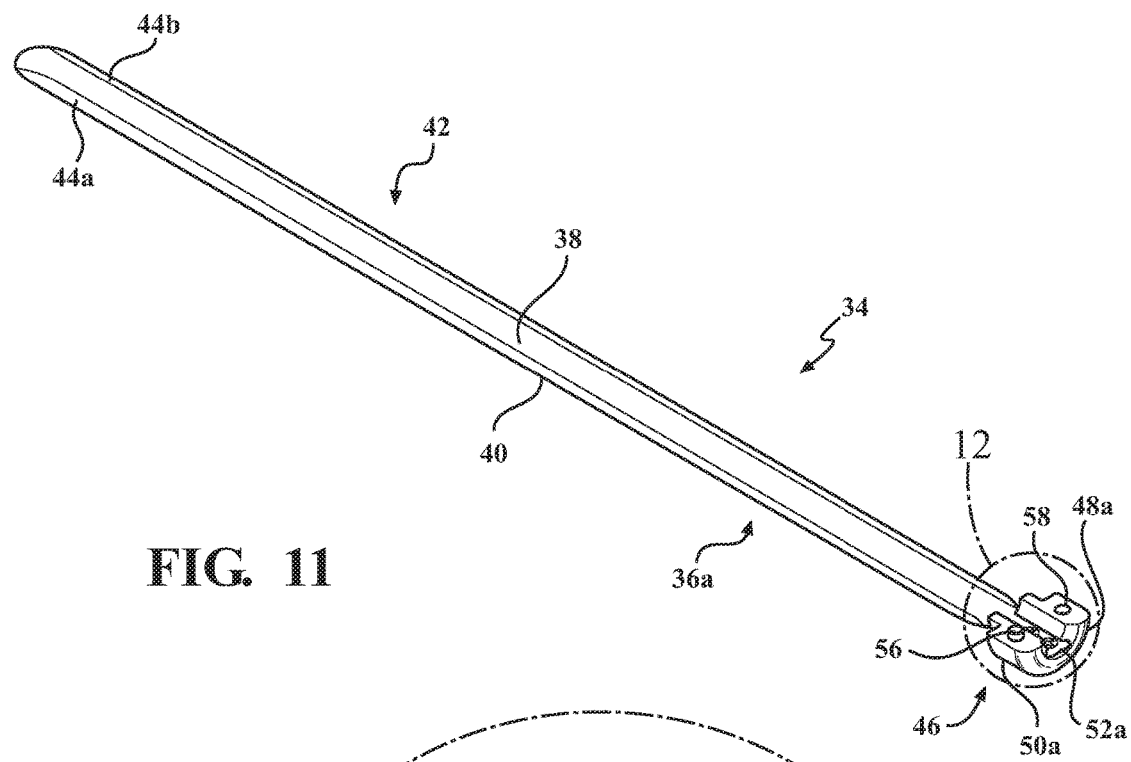
FIG. 11 is an alternative embodiment of a clasping mechanism.
Figure 12:
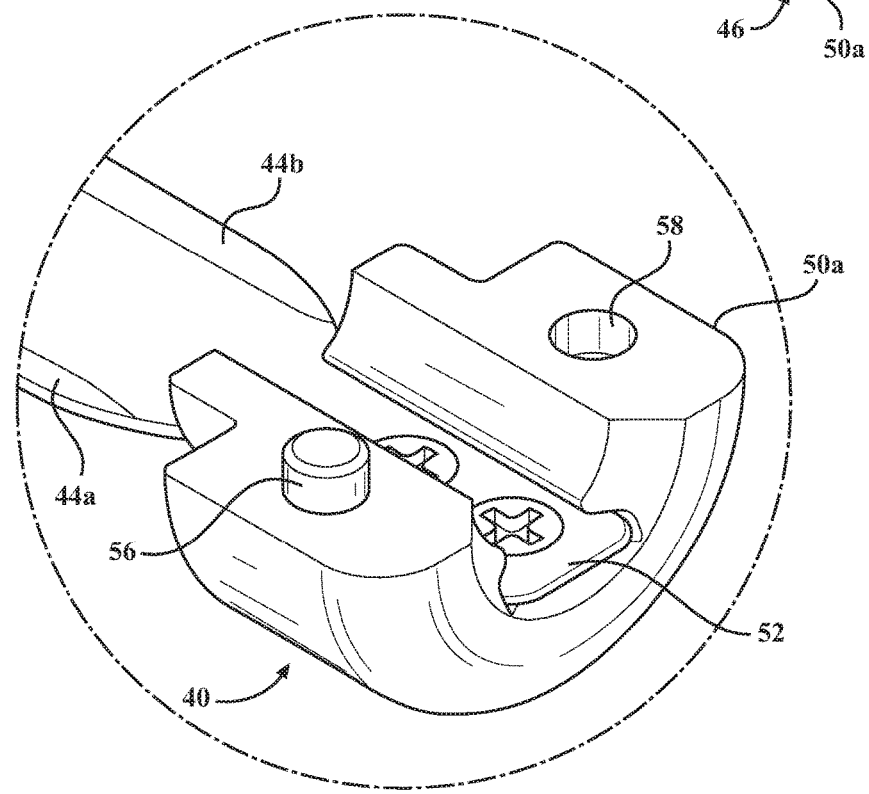
FIG. 12 is an isolated view of the clasping mechanism shown in FIG. 11.

FIGS. 11 and 12 provide an alternative embodiment of the clasping members 48*a*, 48*b*. Mating or inner surfaces of the first and second cylindrical body portions 50*a*, 50*b* (only first cylindrical body portions 50*a* shown) include a peg 56 and an opening 58. The peg 56 may be magnetic and the cylindrical body may be formed of a material configured to emit a magnetic field. Accordingly the peg 56 may be magnetically engaged to a corresponding opening 58. It should be appreciated that only one half of the clasping mechanism 46 is shown, that is clasping member 48*a*, but that clasping member 48*b* is symmetrical to clasping member 48a and thus an explanation of clasping member 48a is sufficient to describe clasping member 48b.

Figure 9A:
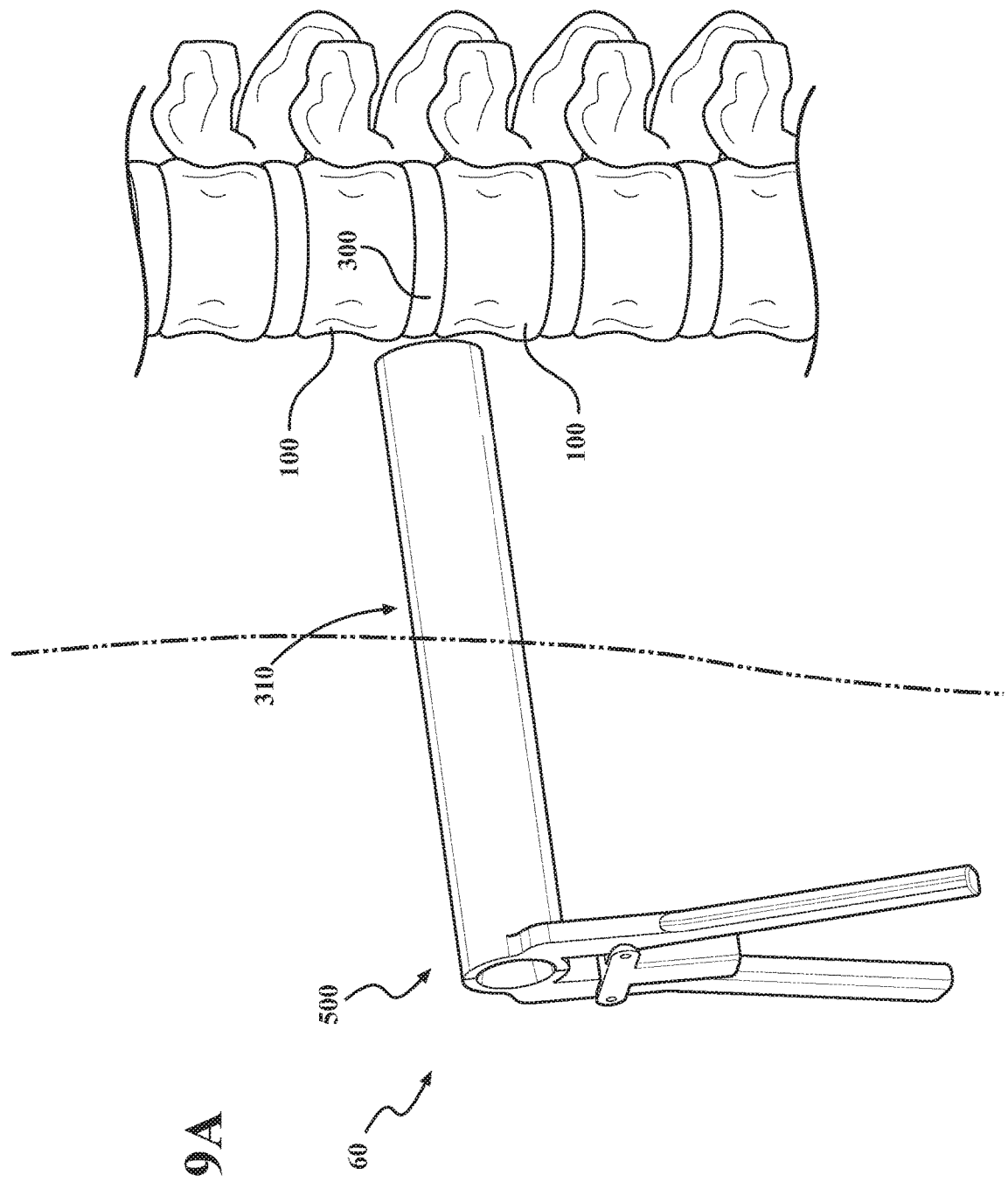
FIG. 9A is a view of a retractor forming a surgical corridor.

With reference now to FIGS. 9A-9E, a system 60 for performing a minimally invasive spinal procedure wherein an implant 10 is introduced into a surgical site 300 is provided. The system 60 includes an instrument 500 configured to create a surgical corridor 310, as shown in FIG. 9A. Such instruments 500 are currently known and used and illustratively include a retractor, which may also be referenced herein as retractor 500.

The system 60 further includes an implant 10 illustratively shown in FIGS. 9B-9E and also FIGS. 1-4. The implant 10 includes an implant body 12 having a superior surface 14 and an inferior surface 16. A pair of grooves 28 are disposed on both the superior and inferior surfaces 14, 16. The grooves 28 are opposite each other and extend the length of the implant body 12. The distal end of the implant 10 may be tapered so as to facilitate the insertion of the implant 10 between adjacent vertebrae 100 at the surgical site 300.

The system further includes a guide 34 having a pair of guide members 36a, 36b. The guide members 36a, 36b have an elongated body 42. The inner surface 38 of the elongated body 42 defines the surgical corridor 310. A pair of ribs 44a, 44b extend axially on opposite sides of the inner surface 38 of the elongated bodies 42. The ribs 44a, 44b are configured to slidingly engage respective grooves 28 of the implant 10.

With reference now to FIG. 9B, the guide 34 with the implant 10 is inserted into the surgical corridor 310 formed by the instrument 500. The implant 10 is placed between the guide members 36a, 36b wherein the ribs 44a, 44b are aligned to engage respective grooves 28. The instrument 500 may then be removed from the body, wherein the muscles are free to close the distal end of the guide members 36a, 36b towards each other with a surgical corridor 320 provided by the guide 34 with guide members 36a, 36b.

The system 60 may further include an inserter 400 wherein the inserter 400 is configured to push the implant 10 down the surgical corridor 320 between guide members 36a, 36b to the surgical site 300, as shown in FIGS. 9B-9E. FIG. 9B shows the inserter 400 engaged with the implant 10 and the implant 10 disposed between guide members 36a, 36b. The grooves 28 of the implant 10 are received by the ribs 44a, 44b of the respective guide members 36 so as to control the axial movement of the implant 10 down the surgical corridor 320 to the surgical site 300.

FIGS. 9C-9E show the instrument 500 removed from the surgical site, thus reducing the size of the surgical corridor 310 (shown in FIGS. 9A and 9B) down to the size of the surgical corridor 320. In particular, the retractor 500, shown in FIGS. 9A and 9B, maintains a generally cylindrical shaped surgical corridor 310 as the retractor blades are formed by a durable and rigid material such as titanium and the ends of the blades are pressed against each other. Accordingly, with the retractor 500 removed, the muscles close in on the guide 34. In particular, musculature load compresses the guide members 36a, 36b together minimizing the size of the surgical corridor 320. Further, as the implant 10 is pushed towards the surgical site 300, the guide members 36a, 36b overcome the musculature load, opening the surgical corridor 320 as the implant 10 moves towards the surgical site 300, as shown in FIGS. 9C-9E.

Figure 13:
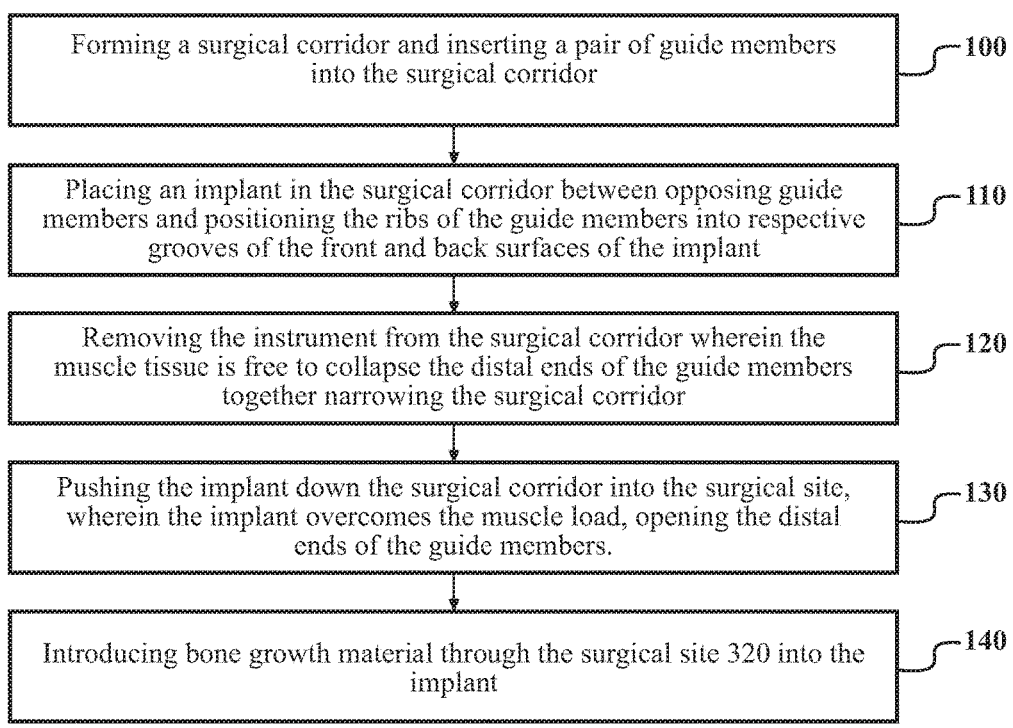
FIG. 13 is a diagram showing a method of inserting an implant into a surgical site.

With reference now to FIG. 13, a method 62 of inserting an implant 10 into a surgical site 300 is also provided. The surgical site 300 is disposed between two vertebrae 100. The surgical corridor 310 is formed by an instrument 500 such as a retractor 500. The method 62 includes an implant 10. The implant 10 includes an implant body 12 having a superior surface 14 and an inferior surface 16. A pair of grooves 28 are disposed on both the superior and inferior surfaces 14, 16. The grooves 28 are opposite each other and extend the length of the implant body 12. The distal end of the implant 10 may be tapered so as to facilitate the insertion of the implant 10 between adjacent vertebrae 100 at the surgical site 300.

The method 62 further includes a guide 34 having a pair of guide members 36a, 36b. The guide members 36a, 36b have an elongated body 42. The inner surface 38 of the elongated body 42 defines the surgical corridor 320. A pair of ribs 44a, 44b extend axially on opposite sides of the inner surface 38 of the elongated bodies 42. The ribs 44a, 44b are configured to slidingly engage respective grooves 28 of the implant 10.

The method begins with step 100 of forming the surgical corridor 310 using the instrument 500. It should be appreciated that other instruments such as a dilator may be used to create an initial opening which is gradually expanded until the retractor 500 is inserted into the surgical corridor 310. The method proceeds by inserting the pair of guide members 36a, 36b into the surgical corridor 310 wherein the clasping members of the guide members 36 hold the proximal ends of the guide members 36a, 36b together so as to space the distal ends of the guide members 36a, 36b apart forming a generally uniform surgical corridor 310 uniform in dimension along the axis of the corridor.

The method 62 proceeds to step 110 of placing an implant 10 in the surgical corridor 310 between opposing guide members 36a, 36b and positioning the ribs 44a, 44b of the guide members 36 into respective grooves 28 of the superior and inferior surfaces 14, 16 of the implant 10. It should be appreciated that the guide 34 may be placed within the surgical corridor 310 formed by the retractor 500 with the implant 10 between guide members 36a, 36b or the implant 10 is inserted between guide members 36a, 36b after the guide 34 is inserted into the surgical corridor 310. The method 62 proceeds to step 120 of removing the instrument 500 (retractor) from the surgical corridor 310 wherein the muscle tissue is free to collapse the distal ends of the guide members 36a, 36b together narrowing the surgical corridor 310 formed by the retractor 500. That is, removal of the instrument 500 collapses the surgical corridor 310 down to surgical corridor 320 provided by the guide members 36a, 36b.

The method proceeds to step 130 of pushing the implant 10 down the surgical corridor 320. The implant 10 may be pushed down the surgical corridor 320 with an inserter rod 400 wherein the inserter rod 400 is positioned through the through hole 52 formed by the clasping mechanism 46 wherein the pressure from the muscle tissue narrows the surgical corridor 310 formed by the guide members 36a, 36b as the implant 10 is pushed past the guide members 36a, 36b as shown in FIG. 9E. The implant 10 is introduced into the surgical site 300 as shown in FIG. 9E. The method may further include step 140 of introducing bone growth material into the implant 10. Accordingly, the method removes the retractor 500 and utilizes a guide 34 to insert the implant 10 thus preventing the muscles from being in an expanded state longer relative to the use of retractors and thus minimizing recovery time for the patient.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. For instance, the implant may have one groove extending axially along adjacent sides if the superior and inferior surface of implant and not a pair of grooves. In such an embodiment, the guide may have guide members each having only one rib so as to guide the implant towards the surgical site along respective grooves. Alternatively, the implant may have only one groove, and the guide may have a pair of guide members, for which only one guide member has a rib working in concert with the groove so as to guide the implant towards the surgical site. It should also be noted that the instrument, system and method described herein is illustrated in an anterior approach, but that the instrument, system and method described herein may be used in other surgical procedures to include a lateral or posterior approach.

I claim:

1. A system for performing a minimally invasive spinal procedure, the system including an instrument configured to create a surgical corridor, the system comprising:
   an implant having an implant body, the implant body having a superior surface opposite an inferior surface, a pair of grooves disposed on the superior surface and another pair of grooves disposed on the inferior surface, each of the pair of grooves having a depth extending radially into respective superior and inferior surfaces, and each of the grooves in the pair of grooves is spaced apart from each other;
   a guide having a pair of guide members, each of the pair of guide members having an elongated body, each of the elongated bodies having an inner surface defining the surgical corridor, each of the pair of guide members further including a pair of ribs extending axially along a respective elongated body, the ribs having a radius greater than the depth of a respective one of the pair of grooves, wherein the ribs are configured to slidingly engage the groove of the implant disposed on the superior and inferior surfaces such that the superior and inferior surfaces of the implant are not in contact with the inner surface of the guide members; and
   a clasping mechanism disposed on a proximal end of the guide, the clasping mechanism including a pair of clasping members and configured to detach from each other and space the proximal ends of the guide members away from each other, each of the pair of clasping members including one half of a concentric bore so as to form a through hole when the pair of clasping members are engaged.

2. The system as set forth in claim 1, wherein each groove of the pair of grooves are spaced apart and parallel to each other.

3. The system as set forth in claim 2, wherein the pair of clasping members comprise a first cylindrical body portion defining generally one half of a cylindrical body having a first through hole portion and a second cylindrical body portion defining generally another half of the cylindrical body having a second through hole portion.

4. The system as set forth in claim 3, wherein each of the pair of clasping members further includes a spacer extending from an inner concave portion of the respective first and second cylindrical body portions, each spacer configured to abut against opposing surfaces of the respective first and second cylindrical body portions so as to maintain the proximal ends of the guide members spaced apart from each other and allow distal ends of the guide members to close in on each other.

* * * * *